United States Patent
Uchida et al.

(10) Patent No.: US 10,716,763 B2
(45) Date of Patent: Jul. 21, 2020

(54) TRANSDERMAL PATCH CONTAINING ROPINIROLE

(71) Applicant: HISAMITSU PHARMACEUTICAL CO., INC., Tosu-shi, Saga (JP)

(72) Inventors: Naoyuki Uchida, Tsukuba (JP); Yasunari Michinaka, Tsukuba (JP)

(73) Assignee: HISAMITSU PHARMACEUTICAL CO., INC., Tosu-Shi, Saga (JP)

(*) Notice: Subject to any disclaimer, the term of this patent is extended or adjusted under 35 U.S.C. 154(b) by 0 days.

(21) Appl. No.: 15/565,864

(22) PCT Filed: Apr. 15, 2016

(86) PCT No.: PCT/JP2016/062105
§ 371 (c)(1),
(2) Date: Oct. 11, 2017

(87) PCT Pub. No.: WO2016/167345
PCT Pub. Date: Oct. 20, 2016

(65) Prior Publication Data
US 2018/0055783 A1 Mar. 1, 2018

(30) Foreign Application Priority Data

Apr. 15, 2015 (JP) ................................. 2015-083216

(51) Int. Cl.
*A61K 9/70* (2006.01)
*A61K 47/18* (2017.01)
*A61K 31/4045* (2006.01)

(52) U.S. Cl.
CPC .......... *A61K 9/7053* (2013.01); *A61K 9/7061* (2013.01); *A61K 9/7069* (2013.01); *A61K 31/4045* (2013.01); *A61K 47/18* (2013.01)

(58) Field of Classification Search
CPC ... A61K 9/7053; A61K 9/7061; A61K 9/7069
See application file for complete search history.

(56) References Cited

U.S. PATENT DOCUMENTS

| | | | |
|---|---|---|---|
| 2005/0074487 A1* | 4/2005 | Hsu | A61K 8/0208 424/448 |
| 2008/0004329 A1 | 1/2008 | Jamieson et al. | |
| 2011/0195109 A1 | 8/2011 | Michinaka et al. | |
| 2012/0052113 A1 | 3/2012 | Uchida et al. | |
| 2013/0195957 A1 | 8/2013 | Shinoda et al. | |
| 2014/0112974 A1 | 4/2014 | Takagi et al. | |
| 2014/0170205 A1 | 6/2014 | Uchida et al. | |
| 2014/0179734 A1 | 6/2014 | Kamakura et al. | |
| 2015/0004215 A1 | 1/2015 | Yoshizaki et al. | |
| 2015/0017226 A1 | 1/2015 | Shibata et al. | |

FOREIGN PATENT DOCUMENTS

| | | |
|---|---|---|
| CN | 101254161 A | 9/2008 |
| CN | 102361638 A | 2/2012 |
| CN | 103153294 A | 6/2013 |
| CN | 103561737 A | 2/2014 |
| EP | 2561865 A2 | 2/2013 |
| JP | H11-506462 A | 6/1999 |
| JP | 2001-518058 A | 10/2001 |
| JP | 2009-542657 A | 12/2009 |
| JP | 5415645 B1 | 11/2013 |
| JP | 2014-231503 | 12/2014 |
| KR | 10-2009-0113351 A | 10/2009 |
| KR | 10-2012-0024562 A | 3/2012 |
| KR | 10-2013-0029035 A | 3/2013 |
| KR | 10-2014-0034814 A | 3/2014 |
| WO | 96/39136 A1 | 12/1996 |
| WO | 97/11696 A1 | 4/1997 |
| WO | 2008/044336 A1 | 4/2008 |
| WO | 2009/107478 A1 | 9/2009 |
| WO | 2012/017892 A1 | 2/2012 |
| WO | 2012/165253 A1 | 12/2012 |
| WO | 2012/165254 A1 | 12/2012 |
| WO | 2013/099835 A1 | 7/2013 |

OTHER PUBLICATIONS

International Preliminary Report on Patentability dated Oct. 17, 2017 issued in corresponding International Application No. PCT/JP2016/062105.
International Search Report dated Jun. 21, 2016 issued in corresponds International Application No. PCT/JP2016/062105.
"Handbook of Pressure Sensitive Adhesive Technology", The Nikkan Kogyo Shinbun, Ltd., 1st edition, 1st print, Mar. 1997, pp. 559-569.
Extended European search report dated Oct. 26, 2018 for corresponding application No. 16780136.4.
Notice of Allowance dated Nov. 28, 2018 issued in corresponding Korean Application No. 10-2017-7028839.
Notice of Allowance dated May 7, 2019 issued in corresponding Japanese Application No. P2017-51295.
Mei Ziqiang, China , "Textile Dictionary", Textile & Apparel Press, Jan. 31, 2007, p. 126.
"Practical Manual of Environmental Emergency Response", Office of the Environmental Emergency Command Leading Group of the Ministry of Environmental Protection, China Environmental Science Press, Jun. 30, 2013, p. 337.
Chinese Office Action dated Dec. 31, 2019 corresponding to application No. 201680018360.1.

\* cited by examiner

*Primary Examiner* — John Pak
(74) *Attorney, Agent, or Firm* — Nath, Goldberg & Meyer; Joshua B. Goldberg; Tanya E. Harkins

(57) ABSTRACT

The present invention provides a patch comprising a backing and an adhesive agent layer laminated on the backing, wherein the adhesive agent layer comprises ropinirole or a pharmaceutically acceptable salt thereof, an organic amine or an acid addition salt thereof, and an adhesive agent.

4 Claims, No Drawings

TRANSDERMAL PATCH CONTAINING ROPINIROLE

This is a National Phase Application filed under 35 U.S.C. 371 as a national stage of PCT/JP2016/062105, filed Apr. 15, 2016, an application claiming the benefit of Japanese Application No. 2015-083216, filed Apr. 15, 2015, the content of each of which is hereby incorporated by reference in its entirety.

TECHNICAL FIELD

The present invention relates to a patch containing ropinirole.

BACKGROUND ART

Ropinirole is a compound represented by the following formula (1) and is also referred to as 4-[2-(dipropylamino)ethyl]-2-indolinone. Ropinirole is known as a dopamine D2 receptor agonist and an oral administration formulation containing ropinirole hydrochloride is in particular effective in treating diseases such as Parkinson's disease and restless legs syndrome.

[Chemical Formula 1]

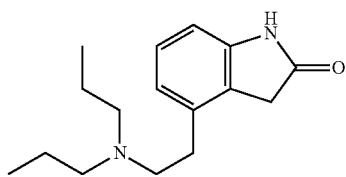

(1)

On the other hand, ropinirole may cause side effects such as somnolence and narcolepsy in response to the increase in a body drug concentration, and the development of a transdermal absorption formulation allowing the administration at a constant rate has been attempted (Patent Literature 1 to 7).

CITATION LIST

Patent Literature

Patent Literature 1: JP 2001-518058 T
Patent Literature 2: JP H11-506462 T
Patent Literature 3: JP 5415645 B
Patent Literature 4: WO 2012/165254 A
Patent Literature 5: WO 2012/165253 A
Patent Literature 6: WO 2009/107478 A
Patent Literature 7: JP 2014-231503 A

SUMMARY OF INVENTION

Technical Problem

The present inventors have found a problem that, in a patch containing ropinirole in an adhesive agent layer, the adhesion force of the patch is gradually reduced during storage. Therefore, an object of the present invention is to provide a patch containing ropinirole or a pharmaceutically acceptable salt thereof, wherein the adhesion force is not reduced even after long storage.

Solution to Problem

The present invention provides a patch comprising a backing and an adhesive agent layer laminated on the backing, wherein the adhesive agent layer comprises ropinirole or a pharmaceutically acceptable salt thereof, an organic amine or an acid addition salt thereof, and an adhesive agent. It is preferable that the organic amine is at least one organic amine selected from the group consisting of monoethanolamine, diethanolamine, triethanolamine, monoisopropanolamine, diisopropanolamine and ethylenediamine. It is preferable that the adhesive agent comprises at least one adhesive agent selected from the group consisting of a rubber adhesive agent, an acrylic adhesive agent and a silicone adhesive agent and in particular it is preferable that the adhesive agent comprises a styrene-isoprene-styrene block copolymer.

Advantageous Effects of Invention

According to the present invention, a patch having excellent storage stability in that adhesiveness of the patch is not reduced over time is provided. With the patch containing ropinirole according to the present invention, ropinirole can be administered at a constant administration rate and therefore the occurrence of side effects can be reduced. Even if side effects occurred, the patch containing ropinirole according to the present invention can be removed easily. Ropinirole tends to be excreted from the kidneys after it is metabolized in the liver, thus, administration of ropinirole can be immediately stopped even if a subject using the patch according to the present invention has a disorder in the liver or the kidneys. The patch containing ropinirole according to the present invention has adhesion force continuing even after long storage and therefore has excellent maintenance of efficacy.

DESCRIPTION OF EMBODIMENTS

The present invention will be described in detail below by illustrating one embodiment.

One embodiment of the present invention is a patch comprising a backing and an adhesive agent layer laminated on the backing, wherein the adhesive agent layer comprises ropinirole or a pharmaceutically acceptable salt thereof, an organic amine or an acid addition salt thereof, and an adhesive agent.

The backing may be any backing as long as it is known to those in the art as a backing of a patch, and may be elastic or non-elastic. When the backing is elastic, the backing is less likely to be separated from skin, because the backing stretches in response to the movement of the skin on which the patch is attached. It is preferable that the material of the backing is specifically polyester such as polyethylene terephthalate (PET), polybutylene terephthalate and polyethylene naphthalate; polyolefin such as polyethylene and polypropylene; nylon; polycarbonate; metal such as aluminium. Examples of the form of the backing include a film, cloth, foil, a porous sheet or a laminated product thereof.

The adhesive agent layer has a preferable adhesive property for skin due to the inclusion of ropinirole or a pharmaceutically acceptable salt thereof, an organic amine or an acid addition salt thereof, and an adhesive agent. It is preferable that the adhesive agent layer is substantially free of water (non-aqueous). Here, "substantially free of water"

means that the concentration of water is 10% or less when the water in the adhesive agent layer is quantified by a Karl-Fischer method.

It is preferable that a pharmaceutically acceptable salt of ropinirole is an acid addition salt of ropinirole. Examples of the acid include a monobasic acid such as hydrochloric acid, hydrobromic acid, acetic acid and methanesulfonic acid; a polybasic acid such as sulfuric acid, fumaric acid, maleic acid, citric acid and tartaric acid. A preferable pharmaceutically acceptable salt of ropinirole is ropinirole hydrochloride.

It is preferable that ropinirole or a pharmaceutically acceptable salt thereof comprises 2 to 30% by mass relative to the total mass of the adhesive agent layer. When a pharmaceutically acceptable salt of ropinirole is used, it is converted to free ropinirole (which is also referred to as "free form") on the calculation of the content. When the content of ropinirole or a pharmaceutically acceptable salt thereof is 2% by mass or more, diseases such as Parkinson's disease and restless legs syndrome can be more effectively treated.

An organic amine is a compound represented by formula (2), wherein $R^1$, $R^2$ and $R^3$ are each independently a hydrogen atom, an optionally substituted alkyl group (preferably, an alkyl group having 1 to 12 carbon atoms) or an optionally substituted aryl group (preferably, an aryl group having 6 to 14 carbon atoms), provided that $R^1$, $R^2$ and $R^3$ are not simultaneously a hydrogen atom. Among $R^1$, $R^2$ and $R^3$, any two can directly bind each other to form a heterocyclic structure or any two can bind through an oxygen atom, a sulfur atom or an imino group (—$NR^4$—) each other to form a heterocyclic structure. $R^4$ is a hydrogen atom, an optionally substituted alkyl group (preferably, an alkyl group having 1 to 12 carbon atoms) or an optionally substituted aryl group (preferably, an aryl group having 6 to 14 carbon atoms). Here, "optionally substituted" means that the group is further substituted with a substituent such as a hydroxy group, an amino group and a thiol group.

[Chemical Formula 2]

(2)

Specific examples of the organic amine include linear or branched alkylamines such as monoethylamine, diethylamine, n-propylamine, isopropylamine, di-n-propylamine, diisopropylamine, triethylamine and ethylenediamine; alkanolamines such as monoethanolamine, di ethanolamine, triethanolamine, monoisopropanolamine, diisopropanolamine, dimethylaminoethanol, trometamol, and meglumine; cyclic amines such as morpholine, piperidine and piperazine; aromatic amines such as aniline and indoline; and polyethyleneimine.

It is more preferable that the organic amine is monoethanolamine, di ethanolamine, triethanolamine, monoisopropanolamine, diisopropanolamine or ethylenediamine. The organic amine can be used alone or in combination of two or more types. It is preferable that the content of the organic amine is 1 to 20% by mass relative to the total mass of the adhesive agent layer.

An acid addition salt of the organic amine can be used instead of the organic amine in the patch of this embodiment.

Examples of the acid added to the organic amine include inorganic acids such as hydrochloric acid, phosphoric acid, sulfuric acid and carbonic acid; organic acids such as formic acid, acetic acid, lactic acid and citric acid. An inorganic acid salt of the organic amine is preferable as the acid addition salt of the organic amine and a hydrochloride salt of the organic amine is more preferable. The adhesion force of the patch becomes less likely to be gradually reduced even during storage of the patch due to the inclusion of an acid addition salt of the organic amine. When the acid addition salt of the organic amine is used, it is converted to the organic amine on the calculation of the content.

Examples of the adhesive agent include a rubber adhesive agent, acrylic adhesive agent, silicone adhesive agent or a mixture thereof. It is preferable that the adhesive agent is substantially free of water. It is preferable that the adhesive agent comprises the rubber adhesive agent in that the rubber adhesive agent has strong cohesion and can suppress the plasticizing action of the adhesive agent by containing ropinirole or a pharmaceutically acceptable salt thereof and organic amine. When the adhesive agent comprises the acrylic adhesive agent or the silicone adhesive agent, there is a tendency that the incidence in which a part of the adhesive agent layer is separated and left on skin on the removal of the patch of this embodiment is more diminished.

The content of the adhesive agent is 30 to 95% by mass and is preferably 50 to 95% by mass relative to the total mass of the adhesive agent layer.

Examples of the rubber adhesive agent include a styrene-isoprene-styrene block copolymer (SIS), isoprene rubber, polyisobutylene (PIB), a styrene-butadiene-styrene block copolymer (SBS), styrene butadiene rubber (SBR) and natural rubber. It is preferable that the rubber adhesive agent comprises the styrene-isoprene-styrene block copolymer (SIS) or polyisobutylene (PIB). Specific examples of the rubber adhesive agent includes Oppanol B12, B15, B50, B80, B100, B120, B150 and B220 (trade name, from BASF), JSR butyl 065, 268 and 365 (trade name, from JSR Corporation), Vistanex LM-MS, MH, H, MML-80, 100, 120 and 140 (trade name, from Exxon Chemicals), HYCAR (trade name, from Goodrich), and SIBSTAR T102 (trade name, from Kaneka Corporation). The rubber adhesive agent can be used alone or in combination of two or more types. The content of the rubber adhesive agent is 0 to 98% by mass relative to the total mass of the adhesive agent layer, and it is preferable that the content is 30 to 95% by mass, and it is more preferable that the content is 50 to 95% by mass. When the adhesive agent layer comprises a plasticizer and a tackifier resin, it is preferable that the total of the contents of the rubber adhesive agent, the tackifier resin and the plasticizer is in the range above.

The acrylic adhesive agent is a polymer of (meth)acrylic acid alkyl ester or a copolymer of (meth)acrylic acid alkyl ester and a comonomer. Here, the (meth)acrylic acid alkyl ester refers to acrylic acid alkyl ester and methacrylic acid alkyl ester. The content of the acrylic adhesive agent is 0 to 98% by mass relative to the total mass of the adhesive agent layer, and it is preferable that the content is 30 to 95% by mass, and it is more preferable that the content is 50 to 95% by mass.

Examples of the (meth)acrylic acid alkyl ester include butyl (meth)acrylate, isobutyl (meth)acrylate, hexyl (meth)acrylate, octyl (meth)acrylate, 2-ethylhexyl (meth)acrylate, and decyl (meth)acrylate. A polymer of one type of the (meth)acrylic acid alkyl ester can be used or a copolymer of two or more types of the (meth)acrylic acid alkyl ester can be used as the acrylic adhesive agent.

Examples of the comonomer include hydroxyalkyl (meth) acrylate, ethylene, propylene, styrene, vinyl acetate, N-vinylpyrrolidone, and (meth)acrylic amide. The comonomer can be used alone or in combination of two or more types.

Specific examples of the acrylic adhesive agent include an acrylic acid-acrylic acid octyl ester copolymer, a 2-ethylhexyl acrylate-vinylpyrrolidone copolymer solution, an acrylic acid ester-vinyl acetate copolymer, a 2-ethylhexyl acrylate-2-ethylhexyl methacrylate-dodecyl methacrylate copolymer, a methyl acrylate-2-ethylhexyl acrylate copolymer resin emulsion, and an acrylic polymer contained in acrylic resin alkanolamine solution. Specific examples of such acrylic adhesive agents include a series of DURO-TAK such as DURO-TAK (registered trademark) 387-2510, DURO-TAK (registered trademark) 87-2510, DURO-TAK (registered trademark) 387-2287, DURO-TAK (registered trademark) 87-2287, DURO-TAK (registered trademark) 87-4287, DURO-TAK (registered trademark) 387-2516, DURO-TAK (registered trademark) 87-2516, DURO-TAK (registered trademark) 87-2074, DURO-TAK (registered trademark) 87-900A, DURO-TAK (registered trademark) 87-901A, DURO-TAK (registered trademark) 87-9301 and DURO-TAK (registered trademark) 87-4098 (from National Starch and Chemical Company); a series of GELVA such as GELVA (registered trademark) GMS 788, GELVA (registered trademark) GMS 3083 and GELVA (registered trademark) GMS 3253 (from Henkel); a series of MAS such as MAS811 (trade name) and MAS683 (trade name) (from CosMED); a series of EUDRAGIT (from HIGUCHI INC.), NIKASOL (from NIPPON CARBIDE INDUSTRIES CO., INC.) and ULTRASOL (from Aica Kogyo Co., Ltd.).

The silicone adhesive agent has an organopolysiloxane backbone and includes dimethyl polysiloxane, polymethylvinylsiloxane and polymethylphenylsiloxane. Examples of the silicone adhesive agent include a series of MD such as MD7-4502 Silicone Adhesive and MD7-4602 Silicone Adhesive (from Dow Corning); a series of BIO-PSA such as BIO-PSA 7-4301 Silicone Adhesive, BIO-PSA 7-4302 Silicone Adhesive, BIO-PSA 7-4201 Silicone Adhesive, BIO-PSA 7-4202 Silicone Adhesive, BIO-PSA 7-4101 Silicone Adhesive, BIO-PSA 7-4102 Silicone Adhesive, BIO-PSA 7-4601 Silicone Adhesive, BIO-PSA 7-4602 Silicone Adhesive, BIO-PSA 7-4501 Silicone Adhesive, BIO-PSA 7-4502 Silicone Adhesive, BIO-PSA 7-4401 Silicone Adhesive, BIO-PSA 7-4402 Silicone Adhesive, 7-9800A, 7-9800B, 7-9700A and 7-9700B (from Dow Corning). The content of the silicone adhesive agent is 0 to 98% by mass relative to the total mass of the adhesive agent layer, and it is preferable that the content is 30 to 95% by mass, and it is more preferable that the content is 50 to 95% by mass.

The adhesive agent layer may further contain additives such as tackifier resin, a plasticizer, a percutaneous absorption promoting agent, a preservative, an ultraviolet absorbing agent, a filler and a flavor. The adhesive agent layer may further contain agents which can be combined with ropinirole or a pharmaceutically acceptable salt thereof in treatment. Examples of the agents include L-dopa and a dopamine D2 receptor agonist.

The tackifier resin is resin which can give adhesion force to the adhesive agent layer. Examples of the tackifier resin include a rosin derivative, alicyclic saturated hydrocarbon resin, aliphatic hydrocarbon resin, terpene, resin and maleic acid copolymer resin. Specific examples of the tackifier include rosin resin such as Ester gum (from Arakawa Chemical Industries, Ltd., trade name), HARIESTER (from Harima Chemicals Group, Inc., trade name), Pentalyn (registered trademark, from Eastman Chemical Company, trade name), Foral (from Eastman Chemical Company, trade name) and KE-311 (from Arakawa Chemical Industries, Ltd., trade name); terpene resin such as YS Resin (from YASUHARA CHEMICAL CO., LID., trade name) and Piccolyte (from Ruth and Dilworth, trade name); petroleum resin such as Arkon (registered trademark, from Arakawa Chemical Industries, Ltd., trade name), Regalrez (from Eastman Chemical Company, trade name), Piccolastic (from Eastman Chemical Company, trade name), Escorez (from Exxon, trade name), Wing Tack (from Goodyear, trade name) and Quintone (registered trademark, from Nippon Zeon, trade name); alicyclic hydrocarbon resin such as phenol resin and xylene resin, and the tackifier resin can be used alone or in combination of two or more types.

When the adhesive agent comprises the rubber adhesive agent, it is preferable that the content of the tackifier resin is 0 to 80% by mass relative to the total mass of the adhesive agent layer, and it is more preferable that the content is 0 to 65% by mass. When the adhesive agent comprises the acrylic adhesive agent, it is preferable that the content of the tackifier resin is 0 to 40% by mass relative to the total mass of the adhesive agent layer, and it is more preferable that the content is 0 to 35% by mass. When the adhesive agent comprises the silicone adhesive agent, it is preferable that the content of the tackifier resin is 0 to 40% by mass relative to the total mass of the adhesive agent layer, and it is more preferable that the content is 0 to 35% by mass.

The plasticizer may be any plasticizer as long as it gives flexibility to the adhesive agent layer. Examples of the plasticizer include a mineral oil (for example, paraffin oil, naphthenic oil and aromatic oil), an animal oil (for example, squalane and squalene), a plant oil (for example, olive oil, camellia oil, castor oil, tall oil and arachis oil), a silicone oil, a dibasic acid ester (for example, dibutyl phthalate and dioctyl phthalate), a liquid rubber (for example, liquid polybutene and liquid polyisoprene), a liquid fatty ester (for example, isopropyl myristate, hexyl laurate, diethyl sebacate and diisopropyl sebacate), a polyalcohol (for example, diethylene glycol, polyethylene glycol, propylene glycol and dipropylene glycol), triacetin, triethyl citrate and crotamiton. The plasticizer can be used alone or in combination of two or more types.

When the adhesive agent is the rubber adhesive agent, it is preferable that the content of the plasticizer is 0 to 70% by mass relative to the total mass of the adhesive agent layer, and it is more preferable that the content is 0 to 35% by mass. When the adhesive agent is the acrylic adhesive agent, it is preferable that the content of the plasticizer is 0 to 50% by mass relative to the total mass of the adhesive agent layer, and it is more preferable that the content is 0 to 30% by mass. When the adhesive agent is the silicone adhesive agent, it is preferable that the content of the plasticizer is 0 to 50% by mass relative to the total mass of the adhesive agent layer, and it is more preferable that the content is 0 to 25% by mass.

The percutaneous absorption promoting agent may be any percutaneous absorption promoting agent as long as it promotes the percutaneous absorption of ropinirole or a pharmaceutically acceptable salt thereof. As the absorption promoting agent, aliphatic alcohols such as isostearyl alcohol, fatty acids such as capric acid, fatty acid derivatives such as propylene glycol monolaurate, isopropyl palmitate and isopropyl myristate, propylene glycol, polyethylene glycol and lauric acid diethanolamide etc. can be suitably used. Among these, lower alcohol esters of fatty acids such as isopropyl palmitate are particularly preferable. Considering the sufficient permeability and local stimulation etc. of an active ingredient to tissue, it is preferable that the content of the absorption promoting agent is 1 to 30% by mass relative to the total mass of the adhesive agent layer, and it is more preferable that the content is 3 to 20% by mass, and it is further preferable that the content is 5 to 15% by mass.

Preferable examples of the preservative include disodium edetate, tetrasodium edetate, ethyl p-hydroxybenzoate, propyl p-hydroxybenzoate and butyl p-hydroxybenzoate. Examples of the ultraviolet absorbing agent include a p-aminobenzoic acid derivative, an anthranilic acid derivative, a salicylic acid derivative, a coumarin derivative, an amino acid compound, an imidazoline derivative, a pyrimidine derivative and a dioxane derivative.

It is preferable that the thickness of the adhesive agent layer is 30 to 300 μm and it is preferable that the thickness is 35 to 200 μm. The area of the patch may be 1 to 100 $cm^2$ or 3 to 40 $cm^2$.

The patch may comprise a release liner to cover and protect the adhesive agent layer. The release liner is released and removed before use of the patch.

Examples of the material of the release liner include a film of polyester (polyethylene terephthalate, polyethylene naphthalate and polybutylene terephthalate etc.) and polyolefin (polyethylene and polypropylene etc.), and paper.

The surface of the release liner facing the adhesive agent layer can be subjected to separating treatment with silicone and Teflon (registered trademark) etc. By the separating treatment, the release liner can be easily released and removed. The separating treatment with silicone is particularly more preferable and release property is stably continued over time. As the release liner, a polyethylene terephthalate film subjected to the separating treatment with silicone is preferable.

The patch according to this embodiment can be manufactured based on a general manufacturing method of a patch. Examples of the general manufacturing method of a patch include the following method. A given amount of ropinirole or a pharmaceutically acceptable salt thereof, an organic amine or an acid addition salt thereof, and an adhesive agent are mixed to obtain a mixture. Then, the mixture is spread on a backing in layers and a release liner is laminated, or the mixture is spread on a release liner in layers and a backing is laminated to manufacture the patch by processes such as a solvent process, a hot melt process and other processes (roll mixing and Banbury mixer mixing etc.).

In the case of the solvent process, ropinirole or a pharmaceutically acceptable salt thereof, an organic amine or an acid addition salt thereof, an adhesive agent, and an additive as needed are dissolved in an organic solvent, and the obtained solution is applied on a release liner, and then the solvent is removed by drying, and a backing is laminated on the formed adhesive agent layer. The patch can be manufactured by cutting the obtained sheet as appropriate. Examples of the organic solvent include ethyl acetate, butyl acetate, toluene, xylene, cyclohexane, hexane, heptane, ethanol, methanol and isopropanol.

It is preferable that the patch according to this embodiment is enclosed in a packaging bag to store. The packaging bag is not specifically limited as long as it is a packaging bag usually used to package a patch containing an agent. As the packaging bag, a plastic packaging bag, a plastic packaging bag on which a metal layer (for example, an aluminium layer) is formed and a metal packaging bag (for example, an aluminium packaging bag) are preferable.

EXAMPLES

The patch of the present invention will be described more specifically below by Examples. However, the present invention is not limited in any way by the Examples.

Test Example 1: Patches Containing a Rubber Adhesive Agent

The patches of Comparative Example 1 and Examples 1 to 5 were prepared, respectively, according to the description in Table 1. Specifically, the solutions obtained by dissolving the components described in Table 1 in an organic solvent were applied on polyester release liners, and then the solvent was removed by drying to obtain adhesive agent layers. Herein, "SIS adhesive agent" refers to the composition obtained by mixing the components described in Table 2. Then, polyester films (backings) were laminated on the adhesive agent layers and then the obtained sheets were cut as appropriate to obtain the patches. The numerical values in Table 1 refer to values in % by mass. That is, the molar ratio of ropinirole hydrochloride to organic amines is identical in the Examples.

TABLE 1

|  | Comparative Example 1 | Example 1 | Example 2 |
| --- | --- | --- | --- |
| Ropinirole hydrochloride | 5 | 5 | 5 |
| SIS adhesive agent | 95 | 93.73 | 92.76 |
| Isopropanolamine | — | 1.27 | — |
| Diisopropanolamine | — | — | 2.24 |
| Monoethanolamine | — | — | — |
| Triethanolamine | — | — | — |
| Ethylenediamine | — | — | — |
| Total | 100 | 100 | 100 |

|  | Example 3 | Example 4 | Example 5 |
| --- | --- | --- | --- |
| Ropinirole hydrochloride | 5 | 5 | 5 |
| SIS adhesive agent | 93.97 | 92.49 | 94.49 |
| Isopropanolamine | — | — | — |
| Diisopropanolamine | — | — | — |
| Monoethanolamine | 1.03 | — | — |
| Triethanolamine | — | 2.51 | — |
| Ethylenediamine | — | — | 0.51 |
| Total | 100 | 100 | 100 |

TABLE 2

| Component | Parts by mass |
| --- | --- |
| SIS | 70 |
| Tackifier resin | 220 |
| Liquid paraffin | 60 |
| PIB | 30 |

Evaluation (Adhesion Force)

The adhesion force of the obtained patches was measured under the conditions of a contact and peel speed of 120 mm/min, a contact load of 200 $gf/cm^2$ and contact time of 1 second against a stainless probe (5 mmΦ) according to a probe tack method (a method described in JIS Z0237: 1991). The measurement was performed twice for the patches: immediately after manufacturing of the patches (before storage) and after storage of 2 weeks at 60° C. (after storage).

The force required to peel was measured over time and graphs (adhesion force curves) with the force required to peel (unit: gf) on the ordinate and the distance from the start point of peeling (peeling distance) on the abscissa were made. The maximums of the force required to peel were described as the adhesion force (unit: gf) in Table 3.

TABLE 3

|  | Comparative Example 1 | Example 1 | Example 2 |
|---|---|---|---|
| Before storage (gf) | 690 | 550 | 550 |
| After storage (gf) | 580 | 550 | 550 |
| Rate of change (%) | 84 | 101 | 99 |

|  | Example 3 | Example 4 | Example 5 |
|---|---|---|---|
| Before storage (gf) | 520 | 530 | 660 |
| After storage (gf) | 530 | 550 | 640 |
| Rate of change (%) | 102 | 104 | 98 |

While the adhesion force of the patch of Comparative Example 1 significantly decreased after storage of 2 weeks at 60° C., the adhesion force of the patches of Examples 1 to 5 compounded with organic amines decreased less. Specifically, in the patches of Examples 1, 2 and 4, when the areas under the curve of the obtained adhesion force curves were used as adhesion energy (unit: gf·mm) for calculation, the values obtained by dividing the measurement results in the patches after storage by the measurement results in the patches before storage (rate of change (unit: %)) were maintained at 90% or more.

Test Example 2: A Patch Containing a Silicone Adhesive Agent

The patch of Example 6 was prepared according to the description in Table 4. Specifically, the solution obtained by dissolving the components described in Table 4 in an organic solvent was applied on a polyester release liner, and then the solvent was removed by drying to obtain an adhesive agent layer. Then, a polyester film (a backing) was laminated on the adhesive agent layer and then the obtained sheet was cut as appropriate to obtain the patch. BIO-PSA 7-4302 (from Dow Corning) was used as the silicone adhesive agent and the numerical values in Table 4 refer to the mass of solid contents. The numerical values in Table 4 refer to values in % by mass, unless otherwise specified.

TABLE 4

|  | Example 6 |
|---|---|
| Ropinirole hydrochloride | 5 |
| Silicone adhesive agent | 92.49 |
| Triethanolamine | 2.51 |
| Total | 100 |

Evaluation (Adhesion Force)
Evaluation was performed same as Test Example 1. The result is shown in Table 5.

TABLE 5

|  | Example 6 |
|---|---|
| Before storage (gf) | 190 |
| After storage (gf) | 350 |
| Rate of change (%) | 180 |

A preferable tendency was observed that the adhesion force of the patch of Example 6 after storage did not decrease and rather improved compared to the adhesion force before storage.

Test Example 3: A Patch Containing an Acrylic Adhesive Agent

The patch of Example 7 was prepared according to the description in Table 6. Specifically, the solution obtained by dissolving the components described in Table 6 in an organic solvent was applied on a polyester release liner, and then the solvent was removed by drying to obtain an adhesive agent layer. Then, a polyester film (a backing) was laminated on the adhesive agent layer and then the obtained sheet was cut as appropriate to obtain the patch. DURO-TAK 87-4098 (from Henkel) was used as the acrylic adhesive agent and the numerical values in Table 6 refer to the mass of solid contents. The numerical values in Table 6 refer to values in % by mass, unless otherwise specified.

TABLE 6

|  | Example 7 |
|---|---|
| Ropinirole hydrochloride | 5 |
| Acrylic adhesive agent | 92.49 |
| Triethanolamine | 2.51 |
| Total | 100 |

Evaluation (Adhesion Force)
Evaluation was performed same as Test Example 1. The result is shown in Table 7.

TABLE 7

|  | Example 7 |
|---|---|
| Before storage (gf) | 240 |
| After storage (gf) | 400 |
| Rate of change (%) | 169 |

A preferable tendency was observed that the adhesion force of the patch of Example 7 after storage did not decrease and rather improved compared to the adhesion force before storage.

The invention claimed is:
1. A patch comprising:
a backing; and
an adhesive agent layer laminated on the backing,
wherein the adhesive agent layer comprises ropinirole or a pharmaceutically acceptable salt thereof, an organic amine or an acid addition salt thereof, and an adhesive agent,
wherein the adhesive agent is selected from the group consisting of a rubber adhesive agent, an acrylic adhesive agent and a silicone adhesive agent;
wherein the organic amine is a compound represented by the formula (2):

(2)

wherein $R^1$, $R^2$ and $R^3$ are each independently, a hydrogen atom, or an alkyl group having 1 to 12 carbon atoms optionally substituted with one or more hydroxy group(s) or amino group(s) when the adhesive agent is a rubber adhesive agent or an acrylic adhesive agent;

wherein the organic amine is selected from the group consisting of monoethanolamine, monoisopropanolamine, ethylenediamine, meglumine, trometamol, triethanolamine, and a combination thereof when the adhesive agent is a silicone adhesive agent;

wherein the content of the organic amine is 1 to 20% by mass relative to the total mass of the adhesive agent layer; and wherein the content of the adhesive agent is 30 to 95% by mass relative to the total mass of the adhesive agent layer.

2. The patch according to claim 1, wherein the organic amine is selected from the group consisting of monoethanolamine, diethanolamine, triethanolamine, monoisopropanolamine, diisopropanolamine and ethylenediamine when the adhesive agent is a rubber adhesive agent or an acrylic adhesive agent.

3. The patch according to claim 1, wherein the rubber adhesive agent comprises a styrene-isoprene-styrene block copolymer.

4. The patch according to claim 2, wherein the rubber adhesive agent comprises a styrene-isoprene-styrene block copolymer.

* * * * *